United States Patent [19]
Bandman et al.

[11] Patent Number: 5,945,306
[45] Date of Patent: Aug. 31, 1999

[54] RAS PROTEIN

[75] Inventors: Olga Bandman; Jennifer L. Hillman, both of Mountain View; Karl J. Guegler, Menlo Park; Y. Tom Tang, Sunnyvale; Neil C. Corley, Mountain View, all of Calif.

[73] Assignee: Incyte Pharmaceuticals, Inc., Palo Alto, Calif.

[21] Appl. No.: 08/991,946

[22] Filed: Dec. 16, 1997

[51] Int. Cl.$^6$ .......................... C12P 21/06; C07K 14/47; C07H 21/04; C12Q 1/68
[52] U.S. Cl. .................. 435/69.1; 435/6; 435/252.3; 435/320.1; 514/12; 514/44; 530/350; 536/23.5
[58] Field of Search ................ 435/69.1, 320.1, 435/252.3, 6; 514/44, 12; 536/23.5; 530/350

[56] References Cited

PUBLICATIONS

Clark, J. et al. "Selective amplification of additional members of the ADP–ribosylation (ARF) family: Cloning of additional human and Drosophila ARF–like proteins." Proceedings of the National Academy of Sciences, USA (Oct. 1993), vol. 90, pp. 8952–895.

Hariharan, I.K. et al. "Characterization of rho GTPase family homologues in *Drosophila melanogaster*: overexpressing Rho 1 in retinal cells causes a late developmental defect." The EMBO Journal (Jan. 1995), vol. 14, No. 2, pp. 292–302.

Database EMBL–est54/GenBank–est 106, Accession number AA103047, Marra et al., The Washington University–HHMI Mouse EST Project, Oct. 29, 1996.

Database EMBL–est54/GenBank–est 106, Accession No. CO4513, Tanaka et al., Genomics, vol. 35, No. 1, pp. 231–235, Jul. 24, 1996.

Database EMBL–est54/GenBank–est 106, Accession No. AA053742, Hillier et al., The Washington University–Merck EST Project, Sep. 13, 1996.

Tavitian, Armand, "Protéines RAS et protéines apparentées", *C.R. Seances Soc. Biol. Fil*, 189:7–12, (1995), (Summary in English–Article in French).

Icard–Liepkalns, C. et al., "An ADP–ribosylation–factor (ARF)–like protein involved in regulated secretion", *Eur. J. Biochem.*, 246:388–393, (1997), (GI 2062132; GI 2062133).

Hall, A. et al., "Cellular responses regulated by rho–related small GTP–binding proteins", *Philos. Trans. R. Soc. Lond. B (Biol.)*, 340:267–271, (1993).

Murphy, C. et al., "Endosome dynamics regulated by a RHO protein", *Nature*, 384:427–432 (1996), (GI 1702942; GI 1702943).

Hotchin, N.A. and A. Hall, "The Assembly of Integrin Adhesion Complexes Requires Both Extracellular Matrix and Intracellular rho/rac GTPases", *J. Cell Biol.*, 131:1857–1865, (1995).

Icard–Liepkalns, C. et al., (Direct Submission), GenBank Sequence Database (Accession 2062133), National Center for Biotechnology Information, National Library of Medicine, Bethesda, Maryland, 20894, (1997) (GI 2062132; GI 2062133).

Icard–Liepkalns, C. et al., (Direct Submission), GenBank Sequence Database (Accession Y12708), National Center for Biotechnology Information, National Library of Medicine, Bethesda, Maryland, 20894, (1997) (GI 2062132; GI 2062133).

Murphy, C. et al., (Direct Submission), GenBank Sequence Database (Accession 1702943), National Center for Biotechnology Information, National Library of Medicine, Bethesda, Maryland, 20894, (1996) (GI 1702942; GI 1702943).

Murphy, C. et al., (Direct Submission), GenBank Sequence Database (Accession X84325), National Center for Biotechnology Information, National Library of Medicine, Bethesda, Maryland, 20894, (1996) (GI 1702942; GI 1702943).

Ren, M. et al., "In its active form, the GTP–binding protein rab8 interacts with a stress–activated protein kinase", *Proc. Natl. Acad. Sci. USA*, 93:5151–5155, (1996).

*Primary Examiner*—Kawai Lau
*Attorney, Agent, or Firm*—Sheela Mohan-Peterson; Lucy J. Billings; Incyte Pharmaceuticals, Inc.

[57] ABSTRACT

The invention provides two human Ras proteins, referred to collectively as "RAPR" and individually as "RAPR-1" and "RAPR-2", and polynucleotides which identify and encode RAPR. The invention also provides expression vectors, host cells, agonists, antibodies and antagonists. The invention also provides methods for preventing and treating disorders associated with expression of RAPR.

13 Claims, 12 Drawing Sheets

```
                                           9          18          27          36          45          54
5' NCC TAC ACG CTT CCG ACG CGT CCC ACG CGT CCG CTT TAG CCG GGT CCC 63          72          81          90          99         108
GCT AAC TCG GCT ACG GTG TAT CTG CGT CTT TGG TCA GGT TGT TCC TTG GCT AAG 117         126         135         144         153         162
AGG GCA GTC GTC GCG GAC CCA CGC GGT TAG CAA GGC TTA GTG CTC GGG CCG GCC 171         180         189         198         207         216
GCC TTC ACT TCC CTC CCG GCT TTT CCT CCC GAC TTA TCC ACT TTA GGG GCG TCT 225         234         243         252         261         270
CGG AGT GCC GGA GCC CCC GGG GAA GAG CGG GGT GCC GGT GTC CGC TCC GGG CTC 279         288         297         306         315         324
GGA TGG GAA GTG GTG GGA GGA GCG ACC CGG GAT GTT CAG TCT GAT GGC CAG TTG 333         342         351         360         369         378
CTG CGG CTG GTT CAA GCG GTG GCG GGA GCT GTC AGA AAG GTG ACT CTT TTG ATG
                                                                      M
```

FIGURE 1A

```
          387         396         405   414         423         432
GTG GGA CTT GAT AAT GCT GGT AAA ACC GCA ACA AAG GGA ATC CAA GGA GAA
 V   G   L   D   N   A   G   K   T   A   T   K   G   I   Q   G   E 441         450         459   468         477         486
TAC CCT GAA GAT GTA GCT CCT ACT GTT GGA TTT TCA AAA ATT AAC CTT AGA CAA
 Y   P   E   D   V   A   P   T   V   G   F   S   K   I   N   L   R   Q 495         504         513   522         531         540
GGA AAG TTT GAA GTC ACC ATC TTT GAC TTG GGA ATA ATT AGA AGA ATT CGG GGA
 G   K   F   E   V   T   I   F   D   L   G   I   I   R   R   I   R   G 549         558         567   576         585         594
ATC AAG AAT TAC TAT GCT GAA TCC TAT GGG GTA ATA TTT GTT GTG GAT TCC
 I   K   N   Y   Y   A   E   S   Y   G   V   I   F   V   V   D   S 603         612         621   630         639         648
AGT GAT GAA GAG AGA ATG GAA GAG ACA AAA GAG GCT ATG TCA GAA ATG CTA AGA
 S   D   E   E   R   M   E   E   T   K   E   A   M   S   E   M   L   R 657         666         675   684         693         702
CAT CCT AGG ATA TCG GGA AAG CCT ATA TTG TTG GCA AAT AAA CAA GAT AAA
 H   P   R   I   S   G   K   P   I   L   L   A   N   K   Q   D   K 711         720         729   738         747         756
GAA GGA GCT TTA GGA GAA GCT GAT GTC ATT GAA TGT CTA TCT CTG GAA AAA TTG
 E   G   A   L   G   E   A   D   V   I   E   C   L   S   L   E   K   L
```

FIGURE 1B

```
                765             774             783             792             801             810
GTC AAT GAG CAC AAG TGC CTG TGT CAG ATA GAA CCA TGT TCA GCA ATC TCG GGG
 V   N   E   H   K   C   L   C   Q   I   E   P   C   S   A   I   S   G 819             828             837             846             855             864
TAT GGA AAG AAA ATT GAC AAG TCC ATT AAA AAA GGC CTT TAT TGG CTG CTA CAT
 Y   G   K   K   I   D   K   S   I   K   K   G   L   Y   W   L   L   H 873             882             891             900             909             918
GTT ATT GCA AGA GAC TTT GAT GCC TTA AAT GAA CGC ATC CAA AAA GAG ACA ACA
 V   I   A   R   D   F   D   A   L   N   E   R   I   Q   K   E   T   T 927             936             945             954             963             972
GAG CAG CGT GCT CTT GAG GAA CAA GAG AAA CAA GAA CGA GCT GAA CGA GTG CGA
 E   Q   R   A   L   E   E   Q   E   K   Q   E   R   A   E   R   V   R 981             990             999            1008            1017            1026
AAA TTA CGA GAA GAA AGA AAA CAA AAT GAA CAG GAG CAG GCT GAA CTC GAT GGA
 K   L   R   E   E   R   K   Q   N   E   Q   E   Q   A   E   L   D   G 1035            1044            1053            1062            1071            1080
ACC AGT GGT CTG GCT GAG TTG GAC CCA GAA CCA ACG AAT CCT TTC CAG CCA ATA
 T   S   G   L   A   E   L   D   P   E   P   T   N   P   F   Q   P   I 1089            1098            1107            1116            1125            1134
GCA TCT GTA ATC ATT GAG AAT GAA GGA AAA AGG AGG ATC TAA AAA AAA AAA
 A   S   V   I   I   E   N   E   G   K   R   R   I   *
```

FIGURE 1C

```
     1143                1152                1161           1170           1179           1188
GGG  GGG  GCC  CCC  CTT  TTT  TTT  TTT  TTG  GGG  GGG  GGG  ATT  TCC  CCC  TTG 1197                1206                1215           1224           1233           1242
TGG  GGT  TTT  TTT  TTG  GGG  GGG  GGC  CAA  GCC  AAA  AAA  ATG  GTT  CCC  CAC  ACC 1251                1260                1269           1278           1287           1296
GGG  GGC  ATA  AAG  AAT  CCC  CCC  CGC  CTG  TTG  GGA  GAA  ACA  AGG  GGG  GCC  CCC  GGG 1305                1314                1323           1332           1341           1350
GGG  GTT  TTT  TTG  GGG  GAA  AAA  AAT  TCC  CCC  CCC  CGG  GAG  GGG  ATA  TTT  TCC  CGC 1359                1368                1377           1386           1395           1404
CCC  GGG  GTG  GGG  GGC  AAG  ACG  CCC  CCG  ATT  GNA  GGN  CNC  GGT  GTG  CGT  TNT  TGT 1413                1422                1431           1440           1449           1458
GGT  TGG  TTG  TTG  TGT  AGA  GAG  CGC  CCC  TCC  GGA  GGA  GGA  GAG  AGG  CGC  CGC  CCG 1467                1476                1485           1494           1503           1512
CGC  GGT  GGT  TCC  TCC  TCT  GTG  TGG  TTG  TTT  TGG  AGA  GGG  AAG  GGG  TGC  TGC
```

FIGURE 1D

```
     1521          1530          1539          1548          1557          1566
CCC GTG TCG CGC GAA GAA AGC TGG CCT GCT GGA GGC TGT TTG TTA ATG AAC GCT 1575          1584          1593          1602          1611          1620
GGG GGG GGT GGG GGG GCG TGA GTG GTG GCC CCG CGG AAC TTC CCA CCA GGG 3'
```

FIGURE 1E

```
  1   M------------------------VGLDNAGKTATAKGIQGEY     143362
  1   MGLLTILKKMKQKERDVRLLMLGLDNAGKTTILKKFNGED         GI 2062133

21   PEDVAPTVGFSKINLRQGKFEVTIFDLGGGIRIRGIWKNY          143362
 41   VDTISPTLGFNIKTLEHRGFKLNIWDVGGQKSLRSYWRNY          GI 2062133

61   YAESYGVIFVVDSSDEERMEETKEAMSEMLRHPRISGKPI          143362
 81   FESTDGLIWVVDSADRQRMQDCQRELQSLLVEERLAGATL          GI 2062133

101   LVLANKQDKEGALGEADVIECLSLEKLVNEHKCLCQIEPC          143362
121   LIFANKQDLPGALSCNAIQEALELDSIRSHHW---RIQGC          GI 2062133

141   SAISGYGKKIDKSIKKGLYWLLHVIARDFDALNERIQKET          143362
158   SAVTG----EDLLPGIDWLLDDISS---------------          GI 2062133

181   TEQRALEEQEKQERAERVRKLREERKQNEQEQAELDGTSG          143362
179   ---RVFTAD                                        GI 2062133

221   LAELDPEPTNPFQPIASVIIENEGKKRRI                    143362
184                                                    GI 2062133
```

```
                              9             18            27            36            45            54
5' GCG CGC CGC CAG TGC GGG CTC CGG GCA ATG GAT GCC CCC GGG GCC CTG
    A   R   R   Q   C   G   L   R   A   M   D   A   P   G   A   L 63            72            81            90            99           108
   GCC CAG ACC GCC GCC CCC GGT CCG GGC AGG AAG GAG CTG AAG ATC GTG
    A   Q   T   A   A   P   G   P   G   R   K   E   L   K   I   V 117           126           135           144           153           162
   GGC GAC GGC TGC AAG ACC TCG CTG CTC ATG GTG TAC AGC CAG GGC TCC
    G   D   G   C   K   T   S   L   L   M   V   Y   S   Q   G   S 171           180           189           198           207           216
   TTC CCC GAG CAC TAC GCC CCA TCG TCG TTC GAG AAG TAC ACG GCC AGC GTG ACC
    F   P   E   H   Y   A   P   S   S   F   E   K   Y   T   A   S   V   T 225           234           243           252           261           270
   GTT GGC AGC AAG GAG GTG ACC CTG AAC CTC TAC CAG AAC ACG GCC GGG CAA GAA GAC
    V   G   S   K   E   V   T   L   N   L   Y   Q   N   T   A   G   Q   E   D 279           288           297           306           315           324
   TAT GAC CGG CTG CGG CCC CTG TCC TAC CAG AAC ACC CAC CTC GTG CTC ATC TGC
    Y   D   R   L   R   P   L   S   Y   Q   N   T   H   L   V   L   I   C 333           342           351           360           369           378
   TAT GAC GTC ATG AAT CCC ACC AGC TAC GAC AAC GTC CTC ATC AAG TGG TTC CCT
    Y   D   V   M   N   P   T   S   Y   D   N   V   L   I   K   W   F   P
```

```
387         396         405         414         423         432
GAG GTC ACG CAT TTC TGC CGC GGG ATC CCC ATG GTG CTC ATC GGC TGC AAG ACA
 E   V   T   H   F   C   R   G   I   P   M   V   L   I   G   C   K   T 441         450         459         468         477         486
GAC CTG AGG AAG GAC CAG GAG CTG CGG AAG CAG GCC CGG GCC CAG CTG GAG
 D   L   R   K   D   Q   E   L   R   K   Q   A   R   A   Q   L   E 495         504         513         522         531         540
CCC ATC TAC ATG CAG GGC CTG AGC GCC TGC GAA CAG ATC CGA GCT GCT CTC
 P   I   Y   M   Q   G   L   S   A   C   E   Q   I   R   A   A   L 549         558         567         576         585         594
TAC CTG GAA TGT TCC GCC AAG TTT CGG GAG AAT GTG GAG GAC GTC TTC CGG GAG
 Y   L   E   C   S   A   K   F   R   E   N   V   E   D   V   F   R   E 603         612         621         630         639         648
GCC AAG GTG GCT CTC CTG AGC GCT CTG AAG CTG AAG AAG GCG CAA CGG CAG CGC
 A   K   V   A   L   L   S   A   L   K   L   K   K   A   Q   R   Q   R 657         666         675         684         693         702
CGG CTC TGC CTG CTG CTG TGA CCC AGG GCA GAC AGA CCT CAC GAC AGC ACT GAC
 R   L   C   L   L   L   *

711         720         729         738         747         756
AGG GGC CCG GGG GCC CAG GTG CCG ATT GCA CCA GGG AGG CTG CCC CAC CCC GAC
```

FIGURE 3B

```
          765            774            783            792            801            810
CCT CCA GCT CAT GGT GTC TGG GGC CTG CGG CTA GAC TCT TGG AAC ATT CTG GGA 819            828            837            846            855            864
ACT CTC TCC CCC GGC TGG GGC TTT GAC CAA NAA ACT CCC CTC CAG GCT GCC 873            882            891            900            909            918
CCT GGG ACA ATG GGT TGA ATG TTG GGT TCA AGG AGN CCA AGT GTT TTG TTG 927            936            945            954            963            972
TTG GGA CCT TTG AAA AGT GGN CCT TAA ATT CAA AAA GGC CAA ACC NNN AAA NCA 981            990            999            1008           1017           1026
AAA GTT GTT GTT TTT CCC CCA AAA GTT GAA AAG GNN TTN AAA AGT TAA TTG NTT 1035           1044           1053           1062           1071           1080
TTT NAA AAA ATN GAA AAA AAA AGG NNT TAA ATT NTT NGG NAA AAG TTG GGG AAA 1089           1098           1107           1116           1125           1134
AAA ANG GTA AGG ACC CCT TTG GGG AAA ATT TNT TTT CCA AAA GGG GGN NNG
```

FIGURE 3C

```
        1143            1152            1161            1170            1179       1188
GGN CCC CAA AAA AGG NNN TTT TTN CAG NAG CCA GCG CAC TGN TGN TCG TTT TTT 1197            1206            1215            1224            1233       1242
TTT TTT TTT TCA TCA CAG GCA CCC CCC ACC NTN NAG TTT TCT TCC CAC GNG 1251            1260            1269            1278            1287       1296
NNA GAT TTA AGC TTA TNT TCG NAA NTN AAN ANN NTN CTN TNT TNG NTA GGG GCT 1305            1314            1323            1332            1341       1350
NTA CCN TTG ATC TTT TTA ATT TCC CCA NNC TNG ANT CCN TTT TTC TNC CAT TTN 1359            1368            1377            1386            1395       1404
CTT TTT TTC TTT TTC CTC GNG TTN CNC TNT TTN NCN NCA CTT TTT TCC CAT TTT 1413            1422            1431            1440            1449       1458
CTC CTT CTT TCC CNA TNA TAA TTA NAN CTC CGA AGG GGN TTT TAC TTT NTT ATN 1467            1476            1485            1494            1503       1512
CAA TAA TCT TTT GCA TCA ATT ANN CCC CTT TNT CAC CCT CTC ATC CTA TTT NCC
```

FIGURE 3D

5' CTT CNC TCT NNT TTN NTT CTC NNN NGN CAT C 3'
1521

RAS PROTEIN

FIELD OF THE INVENTION

This invention relates to nucleic acid and amino acid sequences of two human Ras proteins and to the use of these sequences in the diagnosis, prevention, and treatment of disorders associated with abnormal cell proliferation and apoptosis.

BACKGROUND OF THE INVENTION

Guanine nucleotide-binding proteins (GTP-binding proteins, or G proteins) participate in a wide range of regulatory functions including metabolism, growth, differentiation, signal transduction, cytoskeletal organization, and intracellular vesicle transport and secretion. These proteins control a diverse sets of regulatory pathways in response to hormones, growth factors, neuromodulators, or other signaling molecules. When these molecules bind to transmembrane receptors, signals are propagated to effector molecules by intracellular signal transducing proteins. Many of these signal transducing proteins are members of the Ras superfamily.

The Ras superfamily is a class of low molecular weight (LMW) GTP-binding proteins which consist of 21–30 kDa polypeptides. These proteins regulate cell growth, cell cycle control, protein secretion, and intracellular vesicle interaction. In particular, the LMW GTP-binding proteins activate cellular proteins by transducing mitogenic signals involved in various cell functions in response to extracellular signals from receptors (Tavitian, A. (1995) C. R. Seances Soc. Biol. Fil. 189:7–12). During this process, the hydrolysis of GTP acts as an energy source as well as an on-off switch for the GTPase activity of the LMW GTP-binding proteins.

The Ras superfamily is comprised of five subfamilies: Ras, Rho, Ran, Rab, and ADP-ribosylation factor (ARF). Specifically, Ras genes are essential in the control of cell proliferation. Mutations in Ras genes have been associated with cancer. Rho proteins control signal transduction in the process of linking receptors of growth factors to actin polymerization which is necessary for cell division. Rab proteins control the translocation of vesicles to and from membranes for protein localization, protein processing, and secretion. Ran proteins are localized to the cell nucleus and play a key role in nuclear protein import, control of DNA synthesis, and cell-cycle progression. ARF and ARF-like proteins participate in a wide variety of cellular functions including vesicle trafficking, exocrine secretion, regulation of phospholipase activity, and endocytosis.

Despite their sequence variations, all five subfamilies of the Ras superfamily share conserved structural features. Four conserved sequence regions (motifs I–IV) have been studied in the LMW GTP-binding proteins. Motif I is the most variable but has the conserved sequence, GXXXXGK. The lysine residue is essential in interacting with the β- and γ-phosphates of GTP. Motif II, III, and IV contain highly conserved sequences of DTAGQ, NKXD, and EXSAX, respectively. Specifically, Motif II regulates the binding of γ-phosphate of GTP; Motif III regulates the binding of GTP; and Motif IV regulates the guanine base of GTP. Most of the membrane-bound LMW GTP-binding proteins generally require a carboxy terminal isoprenyl group for membrane association and biological activity. The isoprenyl group is added posttranslationally through recognition of a terminal cysteine residue alone or a CAAX motif. Additional membrane-binding energy is often provided by either internal palmitoylation or a carboxy terminal cluster of basic amino acids. The LMW GTP-binding proteins also have a variable effector region, located between motifs I and II, which is characterized as the interaction site for guanine nucleotide exchange factors (GEFs) or GTPase-activating proteins (GAPs). GEFs induce the release of GDP from the active form of the G protein, whereas GAPs interact with the inactive form by stimulating the GTPase activity of the G protein.

The ARF subfamily has at least 15 distinct members encompassing both ARF and ARF-like proteins. ARF proteins identified to date exhibit high structural similarity and ADP-ribosylation enhancing activity. In contrast, several ARF-like proteins lack ADP-ribosylation enhancing activity and bind GTP differently. An example of ARF-like proteins is a rat protein, ARL184. ARL184 has been shown to have a molecular weight of 22 kDa and four functional GTP-binding sites (Icard-Liepkalns, C. et al. (1997) Eur. J. Biochem. 246: 388–393). ARL184 is active in both the cytosol and the Golgi apparatus and is closely associated with acetylcholine release, suggesting that ARL184 is a potential regulatory protein associated with $Ca^{2+}$-dependent release of acetylcholine.

A number of Rho GTP-binding proteins have been identified in plasma membrane and cytoplasm. These include RhoA, B and C, and D, rhoG, rac 1 and 2, G25K-A and B, and TC10 (Hall, A. et al. (1993) Philos. Trans. R. Soc. Lond. (Biol.) 340:267–271). All Rho proteins have a CAAX motif which binds a prenyl group and either a palmitoylation site or a basic amino acid-rich region, suggesting their role in membrane-associated functions. In particular, RhoD is a protein which functions in early endosome motility and distribution by inducing rearrangement of actin cytoskeleton and cell surface (Murphy, C. et al. (1996) Nature 384:427–432). During cell adhesion, the Rho proteins are essential for triggering focal complex assembly and integrin-dependent signal transduction (Hotchin, N. A. and Hall, A. (1995) J. Cell Biol. 131:1857–1865).

The discovery of two new human Ras proteins and the polynucleotides which encode them satisfies a need in the art by providing new compositions which are useful in the diagnosis, prevention, and treatment of inflammation and disorders associated with cell proliferation and apoptosis.

SUMMARY OF THE INVENTION

The invention features two substantially purified polypeptides, proteins associated with cell proliferation, referred to collectively as "RAPR" and individually as "RAPR-1" and "RAPR-2". In one aspect, the invention provides a substantially purified polypeptide, RAPR, comprising an amino acid sequence selected from the group consisting of SEQ ID NO:1, SEQ ID NO:3, a fragment of SEQ ID NO:1, and a fragment of SEQ ID NO:3.

The invention further provides a substantially purified variant of RAPR having at least 90% amino acid identity to the amino acid sequences of SEQ ID NO:1, or SEQ ID NO:3, or to a fragment of either of these sequences. The invention also provides an isolated and purified polynucleotide sequence encoding the polypeptide comprising an amino acid sequence selected from the group consisting of SEQ ID NO:1, SEQ ID NO:3, a fragment of SEQ ID NO:1, and a fragment of SEQ ID NO:3. The invention also includes an isolated and purified polynucleotide variant having at least 90% polynucleotide identity to the polynucleotide sequence encoding the polypeptide comprising an amino acid sequence selected from the group consisting of SEQ ID NO:1, SEQ ID NO:3, a fragment of SEQ ID NO:1, and a fragment of SEQ ID NO:3.

Additionally, the invention provides a composition comprising a polynucleotide sequence encoding the polypeptide comprising the amino acid sequence selected from the group consisting of SEQ ID NO:1, SEQ ID NO:3, a fragment of SEQ ID NO:1, and a fragment of SEQ ID NO:3. The invention further provides an isolated and purified polynucleotide sequence which hybridizes under stringent conditions to the polynucleotide sequence encoding the polypeptide comprising an amino acid sequence selected from the group consisting of SEQ ID NO:1, SEQ ID NO:3, a fragment of SEQ ID NO:1, and a fragment of SEQ ID NO:3, as well as an isolated and purified polynucleotide sequence which is complementary to the polynucleotide sequence encoding the polypeptide comprising the amino acid sequence selected from the group consisting of SEQ ID NO:1, SEQ ID NO:3, a fragment of SEQ ID NO:1, and a fragment of SEQ ID NO:3.

The invention also provides an isolated and purified polynucleotide sequence comprising a polynucleotide sequence selected from the group consisting of SEQ ID NO:2, SEQ ID NO:4, a fragment of SEQ ID NO:2, and a fragment of SEQ ID NO:4. The invention further provides an isolated and purified polynucleotide variant having at least 90% polynucleotide identity to the polynucleotide sequence comprising a polynucleotide sequence selected from the group consisting of SEQ ID NO:2, SEQ ID NO:4, a fragment of SEQ ID NO:2, and a fragment of SEQ ID NO:4, as well as an isolated and purified polynucleotide sequence which is complementary to the polynucleotide sequence comprising a polynucleotide sequence selected from the group consisting of SEQ ID NO:2, SEQ ID NO:4, a fragment of SEQ ID NO:2, and a fragment of SEQ ID NO:4.

The invention further provides an expression vector containing at least a fragment of the polynucleotide sequence encoding the polypeptide comprising an amino acid sequence selected from the group consisting of SEQ ID NO:1, SEQ ID NO:3, a fragment of SEQ ID NO:1, and a fragment of SEQ ID NO:3. In another aspect, the expression vector is contained within a host cell.

The invention also provides a method for producing a polypeptide comprising the amino acid sequence of SEQ ID NO:1, SEQ ID NO:3, a fragment of SEQ ID NO:1, or a fragment of SEQ ID NO:3, the method comprising the steps of: (a) culturing the host cell containing an expression vector containing at least a fragment of a polynucleotide sequence encoding RAPR under conditions suitable for the expression of the polypeptide; and (b) recovering the polypeptide from the host cell culture.

The invention also provides a pharmaceutical composition comprising a substantially purified RAPR having the amino acid sequence of SEQ ID NO:1, SEQ ID NO:3, a fragment of SEQ ID NO:1, or a fragment of SEQ ID NO:3 in conjunction with a suitable pharmaceutical carrier.

The invention further includes a purified antibody which binds to a polypeptide comprising the amino acid sequence of SEQ ID NO:1, SEQ ID NO:3, a fragment of SEQ ID NO:1, or a fragment of SEQ ID NO:3, as well as a purified agonist and a purified antagonist to the polypeptide.

The invention also provides a method for preventing or treating a disorder associated with an increase in apoptosis comprising administering to a subject in need of such treatment an effective amount of a pharmaceutical composition comprising purified RAPR.

The invention also provides a method for preventing or treating a cancer comprising administering to a subject in need of such treatment an effective amount of an antagonist of RAPR.

The invention also provides a method for preventing or treating an inflammation comprising administering to a subject in need of such treatment an effective amount of an antagonist of RAPR.

The invention also provides a method for detecting a polynucleotide encoding RAPR in a biological sample containing nucleic acids, the method comprising the steps of: (a) hybridizing the complement of the polynucleotide sequence encoding the polypeptide comprising SEQ ID NO:1, SEQ ID NO:3, a fragment of SEQ ID NO:1, or a fragment of SEQ ID NO:3 to at least one of the nucleic acids of the biological sample, thereby forming a hybridization complex; and (b) detecting the hybridization complex, wherein the presence of the hybridization complex correlates with the presence of a polynucleotide encoding RAPR in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D, and 1E show the amino acid sequence (SEQ ID NO:1) and nucleic acid sequence (SEQ ID NO:2) of RAPR-1. The alignment was produced using MACDNASIS PRO software (Hitachi Software Engineering Co. Ltd. San Bruno, Calif.).

FIG. 2 shows the amino acid sequence alignments between RAPR-1 (143362; SEQ ID NO:1) and a rat ADP-ribosylation factor-like protein, ARL184 (GI 2062133; SEQ ID NO:5), produced using the multisequence alignment program of DNASTAR software DNASTAR Inc., Madison, Wis.).

FIGS. 3A, 3B, 3C, 3D, and 3E show the amino acid sequence (SEQ ID NO:3) and nucleic acid sequence (SEQ ID NO:4) of RAPR-2. The alignment was produced using MACDNASIS PRO software (Hitachi Software Engineering Co. Ltd. San Bruno, Calif.).

FIG. 4 shows the amino acid sequence alignments between RAPR-2 (607908; SEQ ID NO:3) and a mouse Rho protein, RhoD (GI 1702943; SEQ ID NO:6), produced using the multisequence alignment program of DNASTAR software (DNASTAR Inc., Madison, Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

RAPR, as used herein, refers to the amino acid sequences of substantially purified RAPR obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to RAPR, increases or prolongs the duration of the effect of RAPR. Agonists may include proteins, nucleic acids, carbohydrates, or any other molecules which bind to and modulate the effect of RAPR.

An "allele" or "allelic sequence", as used herein, is an alternative form of the gene encoding RAPR. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding RAPR as used herein include those with deletions, insertions, or substitutions of different nucleotides resulting in a polynucleotide that encodes the same or a functionally equivalent RAPR. Included within this definition are polymorphisms which may or may not be readily detectable using a particular oligonucleotide probe of the polynucleotide encoding RAPR, and improper or unexpected hybridization to alleles, with a locus other than the normal chromosomal locus for the polynucleotide sequence encoding RAPR. The encoded protein may also be "altered" and contain deletions, insertions, or substitutions of amino acid residues which produce a silent change and result in a functionally equivalent RAPR. Deliberate amino acid substitutions may be made on the basis of similarity in polarity, charge, solubility, hydrophobicity, hydrophilicity, and/or the amphipathic nature of the residues as long as the biological or immunological activity of RAPR is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of RAPR are preferably about 5 to about 15 amino acids in length and retain the biological activity or the immunologic activity of RAPR. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer a Laboratory Manual*, Cold Spring Harbor Press, Plainview, N.Y.).

The term "antagonist" as used herein, refers to a molecule which, when bound to RAPR, decreases the amount or the duration of the effect of the biological or immunological activity of RAPR. Antagonists may include proteins, nucleic acids, carbohydrates, antibodies or any other molecules which decrease the effect of RAPR.

As used herein, the term "antibody" refers to intact molecules as well as fragments thereof, such as Fab, F(ab')$_2$, and Fv, which are capable of binding the epitopic determinant. Antibodies that bind RAPR polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic RAPR, or any oligopeptide thereof, to induce a specific immune response in appropriate animals or cells and to bind with specific antibodies.

The terms "complementary" or "complementarity", as used herein, refer to the natural binding of polynucleotides by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding RAPR (SEQ ID NO:1 or SEQ ID NO:3) or fragments thereof (e.g., SEQ ID NO:2, SEQ ID NO:4, or fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW fragment assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2, or SEQ ID NO:4 by northern analysis is indicative of the presence of mRNA encoding RAPR in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to RAPR or the encoded RAPR. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10 Kb to 10 Mb in size and contain all of the elements required for stable mitotic chromosome segregation and maintenance (Harrington, J. J. et al. (1997) Nat. Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides arranged on a substrate, such as paper, nylon or other type of membrane, filter, chip, glass slide, or any other suitable solid support.

The term "modulate", as used herein, refers to a change in the activity of RAPR. For example, modulation may cause an increase or a decrease in protein activity, binding characteristics, or any other biological, functional or immunological properties of RAPR.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers","primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and top transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, for example, a protein "comprising at least a portion of the amino acid sequence of SEQ ID NO:1" encompasses the full-length RAPR-1 and fragments thereof.

The term "sample", as used herein, is used in its broadest sense. A biological sample suspected of containing nucleic acid encoding RAPR, or fragments thereof, or RAPR itself may comprise a bodily fluid, extract from a cell, chromosome, organelle, or membrane isolated from a cell, a cell, genomic DNA, RNA, or cDNA (in solution or bound to a solid support, a tissue, a tissue print, and the like).

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 μg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of RAPR, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of two new human proteins associated with cell proliferation (hereinafter collectively referred to as "RAPR"), the polynucleotides encoding RAPR, and the use of these compositions for the diagnosis, prevention, or treatment of disorders associated with abnormal cell proliferation and apoptosis.

Nucleic acids encoding the RAPR-1 of the present invention were first identified in Incyte Clone 143362 from a non-adherent peripheral blood mononuclear cell cDNA library (TLYMNOR01) using a computer search for amino acid sequence alignments. A consensus sequence, SEQ ID NO:2, was derived from the following overlapping and/or extended nucleic acid sequences: Incyte Clones 143362 (TLYMNOR01) and 161143 (ADENINB01), and sequences SAAB00528, SAAC00031, and SAAC00032.

In one embodiment, the invention encompasses a polypeptide, RAPR-1, comprising the amino acid sequence of SEQ ID NO:1, as shown in FIGS. 1A, 1B, 1C, 1D, and 1E. RAPR-1 is 249 amino acids in length and contains a GTP-binding motif encompassing residues G3-T10. RAPR-1 has two potential amidation sites encompassing residues Y146-K149 and E243-K246, three potential casein kinase II phosphorylation sites encompassing residues T43-D46, S73-E76, and S74-E77, one potential myristoylation site encompassing residues G3-G8, and three potential protein kinase C phosphorylation sites encompassing residues T12-K14, S96-K98, and S153-K155. As shown in FIG. 2, RAPR-1 has chemical and structural homology with a rat ADP-ribosylation factor-like protein, ARL184 (GI 2062133; SEQ ID NO:5). In particular, RAPR-1 and Bcl-2 binding component 6 share 37% sequence homology. Northern analysis shows the expression of RAPR-1 in various cDNA libraries, at least 50% of which are immortalized or cancerous, at least 25% of which involve immune response, and at least 25% of which are expressed in fetal/infant tissues or organs.

Nucleic acids encoding the RAPR-2 of the present invention were first identified in Incyte Clone 607908 from a colon tissue cDNA library (COLNNOT01) using a computer search for amino acid sequence alignments. A consensus sequence, SEQ ID NO:4, was derived from the following overlapping and/or extended nucleic acid sequences: Incyte Clones 23542 (ADENINB01), 3032785 (TLYMNOT05), and 607908 (COLNNOT01).

In one embodiment, the invention encompasses a polypeptide, RAPR-2, comprising the amino acid sequence of SEQ ID NO:3, as shown in FIGS. 3A, 3B, 3C, 3D, and 3E. RAPR-2 is 211 amino acids in length and has one prenyl group binding site encompassing residues C208-L211. Similar to other Rho proteins, RAPR-2 has three conserved structural motifs encompassing residues G26-T33, D73-Q77, and C131-L135. RAPR-2 also has one potential amidation site encompassing residues P15-K18; four potential casein kinase II phosphorylation sites encompassing residues S43-E46, S51-E54, T104-D107, and S160-E163; and one potential protein kinase C phosphorylation site encompassing residues S174-K176. As shown in FIG. 4, RAPR-2 has chemical and structural homology with a mouse Rho protein, RhoD (GI 1702943; SEQ ID NO:6). In particular, RAPR-2 and RhoD share 52% sequence homology. Northern analysis shows the expression of RAPR-2 in various cDNA libraries, at least 50% of which are immortalized or cancerous, at least 33% of which involve immune response, and at least 33% of which are expressed in fetal/infant tissues or organs.

The invention also encompasses RAPR variants. A preferred RAPR variant is one which has at least about 80%, more preferably at least about 90%, and most preferably at least about 95% amino acid sequence identity to the RAPR amino acid sequence, and which contains at least one biological, immunological or other functional characteristic or activity of RAPR. A most preferred RAPR variant is one having at least 95% amino acid sequence which encodes RAPR.

The invention also encompasses polynucleotides which encode RAPR. Accordingly, any nucleic acid sequence which encodes the amino acid sequence of RAPR can be used to produce recombinant molecules which express RAPR. In a particular embodiment, the invention encompasses a polynucleotide sequence comprising the sequence of SEQ ID NO:2 which encodes RAPR, as shown in FIGS. 1A, 1B, 1C, 1D, and 1E. In a further embodiment, the invention encompasses a polynucleotide sequence comprising the sequence of SEQ ID NO:4 which encodes RAPR, as shown in FIGS. 3A, 3B, 3C, 3D, and 3E.

The invention also encompasses a variant of a polynucleotide sequence encoding RAPR. In particular, such a variant polynucleotide sequence will have at least about 80%, more preferably at least about 90%, and most preferably at least about 95% polynucleotide sequence identity to the polynucleotide sequence encoding RAPR. A particular aspect of the invention encompasses a variant of SEQ ID NO:2, which has at least about 80%, more preferably at least about 90%, and most preferably at least about 95% polynucleotide sequence identity to SEQ ID NO:2. The invention further encompasses a polynucleotide variant of SEQ ID NO:4 having at least about 80%, more preferably at least about 90%, and most preferably at least about 95% polynucleotide sequence identity to SEQ ID NO:4. Any one of the polynucleotide variants described above can encode an amino acid sequence which contains at least one biological, immunological or other functional characteristic or activity of RAPR.

It will be appreciated by those skilled in the art that as a result of the degeneracy of the genetic code, a multitude of nucleotide sequences encoding RAPR, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring RAPR, and all such variations are to be considered as being specifically disclosed.

Although nucleotide sequences which encode RAPR and its variants are preferably capable of hybridizing to the nucleotide sequence of the naturally occurring RAPR under appropriately selected conditions of stringency, it may be advantageous to produce nucleotide sequences encoding RAPR or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding RAPR and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode RAPR and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding RAPR or any fragment thereof.

Also encompassed by the invention are polynucleotide sequences that are capable of hybridizing to the claimed nucleotide sequences, and, in particular, those shown in SEQ ID NO:2, or SEQ ID NO:4, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system marketed by GIBCO/BRL (Gaithersburg, Md.). Preferably, the process is automated with machines such as the MICROLAB 2200 (Hamilton, Reno, Nev.), Peltier thermal cycler (PTC200; MJ Research, Watertown, Mass.), and the ABI CATALYST and 373 and 377 DNA sequencers (Perkin Elmer).

The nucleic acid sequences encoding RAPR may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode RAPR may be used in recombinant DNA molecules to direct expression of RAPR, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express RAPR.

As will be understood by those of skill in the art, it may be advantageous to produce RAPR-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter RAPR encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding RAPR may be ligated to a heterologous sequence to encode a fusion protein. For example, to screen peptide libraries for inhibitors of RAPR activity, it may be useful to encode a chimeric RAPR protein that can be recognized by a commercially available antibody. A fusion protein may also be engineered to contain a cleavage site located between the RAPR encoding sequence and the heterologous protein sequence, so that RAPR may be cleaved and purified away from the heterologous moiety.

In another embodiment, sequences encoding RAPR may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of RAPR, or a fragment thereof. For example, peptide synthesis can be performed using various solid-phase techniques (Roberge, J. Y. et al. (1995) Science 269:202–204) and automated synthesis may be achieved, for example, using the ABI 431A peptide synthesizer (Perkin Elmer).

The newly synthesized peptide may be substantially purified by preparative high performance liquid chromatography (e.g., Creighton, T. (1983) *Proteins, Structures and Molecular Principles,* WH Freeman and Co., New York, N.Y.). The composition of the synthetic peptides may be confirmed by amino acid analysis or sequencing (e.g., the Edman degradation procedure; Creighton, supra). Additionally, the amino acid sequence of RAPR, or any part thereof, may be altered during direct synthesis and/or combined using chemical methods with sequences from other proteins, or any part thereof, to produce a variant polypeptide.

In order to express a biologically active RAPR, the nucleotide sequences encoding RAPR or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding RAPR and appropriate transcriptional and translational control elements. These methods include in vitro recombinant DNA techniques, synthetic techniques, and in vivo genetic recombination. Such techniques are described in Sambrook, J. et al. (1989; *Molecular Cloning, A Laboratory Manual,* Cold Spring Harbor Press, Plainview, N.Y.), and Ausubel, F. M. et al. (1989; *Current Protocols in Molecular Biology,* John Wiley & Sons, New York, N.Y.).

A variety of expression vector/host systems may be utilized to contain and express sequences encoding RAPR. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus);

plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding RAPR, vectors based on SV40 or EBV may be used with an appropriate selectable marker.

In bacterial systems, a number of expression vectors may be selected depending upon the use intended for RAPR. For example, when large quantities of RAPR are needed for the induction of antibodies, vectors which direct high level expression of fusion proteins that are readily purified may be used. Such vectors include, but are not limited to, the multifunctional $E.$ $coli$ cloning and expression vectors such as BLUESCRIPT (Stratagene), in which the sequence encoding RAPR may be ligated into the vector in frame with sequences for the amino-terminal Met and the subsequent 7 residues of $\beta$-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, $Saccharomyces$ $cerevisiae,$ a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding RAPR may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill $Yearbook$ $of$ $Science$ $and$ $Technology$ (1992) McGraw Hill, New York, N.Y.; pp. 191–196.

An insect system may also be used to express RAPR. For example, in one such system, $Autographa$ $californica$ nuclear polyhedrosis virus (AcNPV) is used as a vector to express foreign genes in $Spodoptera$ $frugiperda$ cells or in Trichoplusia larvae. The sequences encoding RAPR may be cloned into a non-essential region of the virus, such as the polyhedrin gene, and placed under control of the polyhedrin promoter. Successful insertion of RAPR will render the polyhedrin gene inactive and produce recombinant virus lacking coat protein. The recombinant viruses may then be used to infect, for example, $S.$ $frugiperda$ cells or Trichoplusia larvae in which RAPR may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding RAPR may be ligated into an adenovirus transcription/translation complex consisting of the late promoter and tripartite leader sequence. Insertion in a non-essential E1 or E3 region of the viral genome may be used to obtain a viable virus which is capable of expressing RAPR in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10 Mb are constructed and delivered via conventional delivery methods (liposomes, polycationic amino polymers, or vesicles) for therapeutic purposes.

Specific initiation signals may also be used to achieve more efficient translation of sequences encoding RAPR. Such signals include the ATG initiation codon and adjacent sequences. In cases where sequences encoding RAPR, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express RAPR may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr, which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding RAPR is inserted within a marker gene sequence, transformed cells containing sequences encoding RAPR can be identified by the absence of marker gene function. Alternatively, a marker gene can be placed in tandem with a sequence encoding RAPR under the control of a single promoter. Expression of the marker gene in response to induction or selection usually indicates expression of the tandem gene as well.

Alternatively, host cells which contain the nucleic acid sequence encoding RAPR and express RAPR may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of nucleic acid or protein.

The presence of polynucleotide sequences encoding RAPR can be detected by DNA—DNA or DNA-RNA hybridization or amplification using probes or fragments or fragments of polynucleotides encoding RAPR. Nucleic acid amplification based assays involve the use of oligonucleotides or oligomers based on the sequences encoding RAPR to detect transformants containing DNA or RNA encoding RAPR.

A variety of protocols for detecting and measuring the expression of RAPR, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on RAPR is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding RAPR include oligolabeling, nick translation, end-labeling or PCR amplification using a labeled nucleotide. Alternatively, the sequences encoding RAPR, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn (Kalamazoo, Mich.); Promega (Madison, Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding RAPR may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode RAPR may be designed to contain signal sequences which direct secretion of RAPR through a prokaryotic or eukaryotic cell membrane. Other constructions may be used to join sequences encoding RAPR to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and RAPR may be used to facilitate purification. One such expression vector provides for expression of a fusion protein containing RAPR and a nucleic acid encoding 6 histidine residues preceding a thioredoxin or an enterokinase cleavage site. The histidine residues facilitate purification on IMAC (immobilized metal ion affinity chromatography) as described in Porath, J. et al. (1992; Prot. Exp. Purif. 3:263–281) while the enterokinase cleavage site provides a means for purifying RAPR from the fusion protein. A discussion of vectors which contain fusion proteins is provided in Kroll, D. J. et al. (1993; DNA Cell Biol. 12:441453).

In addition to recombinant production, fragments of RAPR may be produced by direct peptide synthesis using solid-phase techniques. (Merrifield S. (1963) J. Am. Chem. Soc. 85:2149–2154). Protein synthesis may be performed using manual techniques or by automation. Automated synthesis may be achieved, for example, using an Applied Biosystems 431A peptide synthesizer (Perkin Elmer). Various fragments of RAPR may be chemically synthesized separately and combined using chemical methods to produce the full length molecule.

THERAPEUTICS

Chemical and structural homology exists between RAPR-1 and a rat ADP-ribosylation factor-like protein, ARL184 (GI 2062133; SEQ ID NO:5) and between RAPR-2 and a mouse Rho protein, RhoD (GI 1702943; SEQ ID NO:6). Northern analysis of RAPR (SEQ ID NO:1 or SEQ ID NO:3) expression suggests an association with cell proliferation, inflammation, and fetal/infant development. Therefore, RAPR appears to play a role in apoptosis, inflammation, and cancer.

In disorders associated with an increase in apoptosis where RAPR inhibits apoptosis, it is desirable to increase the expression of RAPR. Therefore, in one embodiment, RAPR or a fragment or derivative thereof may be administered to a subject to prevent or treat a disorder associated with an increase in apoptosis. Such disorders include, but are not limited to, AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis.

In another embodiment, a pharmaceutical composition comprising RAPR may be administered to a subject to prevent or treat a disorder associated with increased apoptosis including, but not limited to, those listed above.

In still another embodiment, an agonist which is specific for RAPR may be administered to prevent or treat a disorder associated with increased apoptosis including, but not limited to, those listed above.

In a further embodiment, a vector capable of expressing RAPR, or a fragment or a derivative thereof, may be used to prevent or treat a disorder associated with increased apoptosis including, but not limited to, those listed above.

In cancer, where RAPR promotes cell proliferation, it is desirable to decrease its activity. Therefore, in one embodiment, an antagonist of RAPR may be administered to a subject to prevent or treat cancer including, but not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody specific for RAPR may be used directly as an antagonist, or indirectly as a targeting or delivery mechanism for bringing a pharmaceutical agent to cells or tissue which express RAPR.

In another embodiment, a vector expressing the complement of the polynucleotide encoding RAPR may be administered to a subject to prevent or treat a cancer including, but not limited to, the types of cancer listed above.

In inflammation, where RAPR promotes cell proliferation, it is desirable to decrease its activity. Therefore, in one embodiment, an antagonist of RAPR may be administered to a subject to prevent or treat an inflammation. Disorders associated with inflammation include, but are not limited to, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma. In one aspect, an antibody specific for RAPR may be used directly as an antagonist, or indirectly as a targeting or delivery mechanism for bringing a pharmaceutical agent to cells or tissue which express RAPR.

In another embodiment, a vector expressing the complement of the polynucleotide encoding RAPR may be administered to a subject to prevent or treat an inflammation associated with any disorder including, but not limited to, those listed above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of RAPR may be produced using methods which are generally known in the art. In particular, purified RAPR may be used to produce antibodies or to screen libraries of pharmaceutical agents to identify those which specifically bind RAPR.

Antibodies to RAPR may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with RAPR or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to RAPR have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of RAPR amino acids may be fused with those of another protein such as keyhole limpet hemocyanin and antibody produced against the chimeric molecule.

Monoclonal antibodies to RAPR may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454). Alternatively, techniques described for the production of single chain antibodies may be adapted, using methods known in the art, to produce RAPR-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86:3833–3837; Winter, G. et al. (1991) Nature 349:293–299).

Antibody fragments which contain specific binding sites for RAPR may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between RAPR and its specific antibody. A two-site, monoclonal-based immunoassay utilizing monoclonal antibodies reactive to two non-interfering RAPR epitopes is preferred, but a competitive binding assay may also be employed (Maddox, supra).

In another embodiment of the invention, the polynucleotides encoding RAPR, or any fragment or complement thereof, may be used for therapeutic purposes. In one aspect, the complement of the polynucleotide encoding RAPR may be used in situations in which it would be desirable to block the transcription of the MRNA. In particular, cells may be transformed with sequences complementary to polynucleotides encoding RAPR. Thus, complementary molecules or fragments may be used to modulate RAPR activity, or to achieve regulation of gene function. Such technology is now well known in the art, and sense or antisense oligonucleotides or larger fragments, can be designed from various locations along the coding or control regions of sequences encoding RAPR.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding RAPR. These techniques are described both in Sambrook et al. (supra) and in Ausubel et al. (supra).

Genes encoding RAPR can be turned off by transforming a cell or tissue with expression vectors which express high levels of a polynucleotide or fragment thereof which encodes RAPR. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding RAPR (signal sequence, promoters, enhancers, and introns). Oligonucleotides derived from the transcription initiation site, e.g., between positions –10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The complementary sequence or antisense molecule may also be designed to block translation of RNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding RAPR.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding RAPR. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of RAPR, antibodies to RAPR, mimetics, agonists, antagonists, or inhibitors of RAPR. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of RAPR, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example RAPR or fragments thereof, antibodies of RAPR, agonists, antagonists or inhibitors of RAPR, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, which can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind RAPR may be used for the diagnosis of conditions or diseases characterized by expression of RAPR, or in assays to monitor patients being treated with RAPR, agonists, antagonists or inhibitors. The antibodies useful for diagnostic purposes may be prepared in the same manner as those described above for therapeutics. Diagnostic assays for RAPR include methods which utilize the antibody and a label to detect RAPR in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring RAPR are known in the art and provide a basis for diagnosing altered or abnormal levels of RAPR expression. Normal or standard values for RAPR expression are established by combining body fluids or cell extracts taken from normal mammalian subjects, preferably human, with antibody to RAPR under conditions suitable for complex formation The amount of standard complex formation may be quantified by various methods, but preferably by photometric, means. Quantities of RAPR expressed in subject samples from biopsied tissues are compared with the standard values. Deviation between standard and subject values establishes the parameters for diagnosing disease.

In another embodiment of the invention, the polynucleotides encoding RAPR may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of RAPR may be correlated with disease. The diagnostic assay may be used to distinguish between absence, presence, and excess expression of RAPR, and to monitor regulation of RAPR levels during therapeutic intervention.

In one aspect, hybridization with PCR probes which are capable of detecting polynucleotide sequences, including genomic sequences, encoding RAPR or closely related molecules, may be used to identify nucleic acid sequences which encode RAPR. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding RAPR, alleles, or related sequences.

Probes may also be used for the detection of related sequences, and should preferably contain at least 50% of the nucleotides from any of the RAPR encoding sequences. The hybridization probes of the subject invention may be DNA or RNA and derived from the nucleotide sequence of SEQ ID NO:2, SEQ ID NO:4, or from genomic sequence including promoter, enhancer elements, and introns of the naturally occurring RAPR.

Means for producing specific hybridization probes for DNAs encoding RAPR include the cloning of nucleic acid sequences encoding RAPR or RAPR derivatives into vectors for the production of MRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding RAPR may be used for the diagnosis of conditions or disorders which are associated with expression of RAPR. Examples of such conditions or disorders include, but are not limited to, cancers such as adenocarcinoma, leukemia, lymphoma, melanoma, myeloma, sarcoma, and teratocarcinoma, and particularly, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; disorders with associated inflammation such as Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma; disorders with associated apoptosis such as AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis. The polynucleotide sequences encoding RAPR may be used in Southern or northern analysis, dot blot, or other membrane-based technologies; in PCR technologies; or in dipstick, pin, ELISA assays or microarrays utilizing fluids or tissues from patient biopsies to detect altered RAPR expression. Such qualitative or quantitative methods are well known in the art.

In a particular aspect, the nucleotide sequences encoding RAPR may be useful in assays that detect activation or induction of various cancers, particularly those mentioned above. The nucleotide sequences encoding RAPR may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding RAPR in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of RAPR, a normal or standard profile for expression is established. This may be accomplished by combining body fluids or cell extracts taken from normal subjects, either animal or human, with a sequence, or a fragment thereof, which encodes RAPR, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding RAPR may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of RAPR include radiolabeling or biotinylating nucleotides, coamplification of a control nucleic acid, and standard curves onto which the experimental results are interpolated (Melby, P. C. et al. (1993) J. Immunol. Meth., 159:235–244; Duplaa, C. et al. (1993) Anal. Biochem. 212:229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations, and polymorphisms. This information will be useful in determining gene function, understanding the genetic basis of disease, diagnosing disease, and in developing and monitoring the activity of therapeutic agents.

In one embodiment, the microarray is prepared and used according to the methods known in the art such as those described in PCT application WO95/11995 (Chee et al.), Lockhart, D. J. et al. (1996; Nat. Biotech. 14:1675–1680) and Schena, M. et al. (1996; Proc. Natl. Acad. Sci. 93:10614–10619).

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably about 15 to 30 nucleotides in length, and most preferably about 20 to 25 nucleotides in length. For a certain type of microarray, it may be preferable to use oligonucleotides which are only 7 to 10 nucleotides in length. The microarray may contain oligonucleotides which cover the known 5' (or 3') sequence, or may contain sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell or tissue type or to a normal, developmental, or disease state. In certain situations, it may be appropriate to use pairs of oligonucleotides on a microarray. The pairs will be identical, except for one nucleotide preferably located in the center of the sequence. The second oligonucleotide in the pair (mismatched by one) serves as a control. The number of oligonucleotide pairs may range from 2 to 1,000,000.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In one aspect, the oligomers are synthesized at designated areas on a substrate using a light-directed chemical process. The substrate may be paper, nylon or any other type of membrane, filter, chip, glass slide, or any other suitable solid support.

In one aspect, the oligonucleotides may be synthesized on the surface of the substrate by using a chemical coupling procedure and an ink jet application apparatus, such as that described in PCT application WO95/251116 (Baldeschweiler et al.). In another aspect, a "gridded" array analogous to a dot or slot blot (HYBRIDOT apparatus, GIBCO/BRL) may be used to arrange and link cDNA fragments or oligonucleotides to the surface of a substrate using a vacuum system, thermal, UV, mechanical or chemical bonding procedures. In yet another aspect, an array may be produced by hand or by using available devices, materials, and machines (including BRINKMANN multichannel pipettors or robotic instruments) and may contain 8, 24, 96, 384, 1536 or 6144 oligonucleotides, or any other multiple from 2 to 1,000,000 which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs (aRNA) are appropriate probes. Therefore, in one aspect, MRNA is used to produce cDNA which, in turn and in the presence of fluorescent nucleotides, is used to produce fragment or oligonucleotide aRNA probes. These fluorescently labeled probes are incubated with the microarray so that the probe sequences hybridize to the cDNA oligonucleotides of the microarray. In another aspect, nucleic acid sequences used as probes can include polynucleotides, fragments, and complementary or antisense sequences produced using restriction enzymes, PCR technologies, and Oligolabeling or TransProbe kits (Pharmacia) well known in the area of hybridization technology.

Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. A detection system may be used to measure the absence, presence, and amount of hybridization for all of the distinct sequences simultaneously. This data may be used for large scale correlation studies or functional analysis of the sequences, mutations, variants, or polymorphisms among samples (Heller, R. A. et al., (1997) Proc. Natl. Acad. Sci. 94:2150–55).

In another embodiment of the invention, the nucleic acid sequences which encode RAPR may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding RAPR on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, RAPR, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between RAPR and the agent being tested, may be measured.

Another technique for drug screening which may be used provides for high throughput screening of compounds having suitable binding affinity to the protein of interest as described in published PCT application WO84/03564. In this method, as applied to RAPR large numbers of different small test compounds are synthesized on a solid substrate, such as plastic pins or some other surface. The test compounds are reacted with RAPR, or fragments thereof, and washed. Bound RAPR is then detected by methods well known in the art. Purified RAPR can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding RAPR specifically compete with a test compound for binding RAPR. In this manner, the antibodies can be used to detect the presence of any peptide which shares one or more antigenic determinants with RAPR.

In additional embodiments, the nucleotide sequences which encode RAPR may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

The TLYMNOT01 cDNA library was constructed using RNA isolated from non-adherent peripheral blood mononuclear cells obtained from a 24-year-old Caucasian male. The cells were separated, flash frozen, ground in a mortar and pestle, and lyzed immediately in buffer containing guanidinium isothiocyanate. Lysis was followed by phenol chloroform extraction, CsCl separation, and ethanol precipitation. Poly A+ RNA was isolated using biotinylated oligo d(T) primer and streptavidin coupled to a paramagnetic particle (Promega, Madison, Wis.).

cDNA was prepared by Stratagene (La Jolla, Calif.) using random oligo d(T) priming. Double-stranded cDNA was blunted, ligated to EcoRI adaptors, digested with XhoI, size-selected, and cloned into the XhoI and EcoRI sites of the Lambda UNI-ZAP vector system (Stratagene). Subsequently, the custom-constructed library phage particles were infected into E. coli host strain XL1-BLUE (Stratagene).

The COLNNOT01 cDNA library was constructed from the non-tumorous colon tissue obtained from a 75-year-old Caucasian male by hemicolectomy. The pathology report noted the presence of an invasive grade 3 adenocarcinoma in the tumorous portion of the patient's colon. The adenocarcinoma mass arose in a tubulovillous adenoma distal to the ileocecal valve in the cecum, and the tumor penetrated deeply into the muscularis propria but not through it. After reporting blood in his stool, the patient was diagnosed with a malignant neoplasm in the cecum.

The frozen tissue was homogenized and lysed using a Polytron PT-3000 homogenizer (Brinkmann Instruments, Westbury, N.Y.) in guanidinium isothiocyanate solution. The lysate was centrifuged over a 5.7 M CsCl cushion using an SW28 rotor in a L8-70M Ultracentrifuge (Beckman Instruments) for 18 hours at 25,000 rpm at ambient temperature. The RNA was extracted with acid phenol pH 4.0, precipitated using 0.3 M sodium acetate and 2.5 volumes of ethanol, resuspended in RNAse-free water and DNAse treated at 37° C. The RNA extraction and precipitation were repeated as before. The mRNA was then isolated using the OLIGOTEX kit (QIAGEN Inc., Chatsworth, Calif.) and used to construct the cDNA library.

The mRNA was handled according to the recommended protocols in the SUPERSCRIPT plasmid system for cDNA synthesis and plasmid cloning (Cat. #18248-013, Gibco/BRL). cDNAs were fractionated on a SEPHAROSE CL4B column (Cat. #275105-01, Pharmacia), and those cDNAs exceeding 400 bp were ligated into PSPORT. The plasmid PSPORT was subsequently transformed into DH5a™ competent cells (Cat. #18258-012, Gibco/BRL).

II Isolation and Sequencing of cDNA Clones

The phagemid forms for individual TLYMNOT01 cDNA clones were obtained by the in vivo excision process, in which the host bacterial strain was co-infected with both the library phage and an f1 helper phage. Proteins derived from both the lambda phage and f1 helper phage initiated new DNA synthesis from defined sequences on the lambda target DNA to create the smaller, single-stranded circular PBLUESCRIPT phagemid (Stratagene) which contains the TLYMNOT01 inserts. When the phagemid DNA was released from the cells, it was purified and used to reinfect fresh bacterial host cells (SOLR; Stratagene). Transformed bacteria expressing the β-lactamase gene on the phagemid survived selection on medium containing ampicillin and produced double-stranded phagemid.

Phagemid DNA was purified using the QIAWELL-8 plasmid purification system (QIAGEN) and prepared for sequencing. Chain termination reaction products were electrophoresed on urea-polyacrylamide gels and detected by fluorescence.

Plasmid cDNA for COLNNOT01 was released from the cells and purified using the R.E.A.L. PREP 96 plasmid kit (Catalog #26173, QIAGEN). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, GIBCO/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

cDNAs for both libraries were sequenced according to the method of Sanger et al. (1975, J. Mol. Biol. 94:441f), using the Perkin Elmer CATALYST 800 or a MICRO LAB 2200 (Hamilton, Reno, Nev.) in combination with Peltier thermal cyclers (PTC200 from MJ Research, Watertown, Mass.) and Applied Biosystems 377 DNA sequencing systems or the Perkin Elmer 373 DNA sequencing system and the reading frame was determined.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul SF (1993) J. Mol. Evol. 36:290–300; Altschul, SF et al. (1990) J. Mol. Biol. 215:403–10).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R F and T F Smith (1992 Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin and Altschul (1993; Proc Nat Acad Sci 90:5873–7) and incorporated herein by reference, searches matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) J.Mol.Evol. 36:290–300; Altschul, S. F. et al. (1990) J.Mol.Evol. 215:403–410) are used to search for identical or related molecules in nucleotide databases such as GenBank or LIFESEQ (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding RAPR occurs. Abundance and percent abundance are also reported. Abundance directly reflects the number of times a particular transcript is represented in a cDNA library, and percent abundance is abundance divided by the total number of sequences examined in the cDNA library.

V Extension of RAPR Encoding Polynucleotides

The nucleic acid sequence of the Incyte Clone 143362 or 607908 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 software (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (GIBCO/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier thermal cycler (PTC200; M. J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK (QIAGEN), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2–3 hours or overnight at 16° C. Competent E. coli cells (in 40 µl of appropriate media) were transformed with 3 µl of ligation mixture and cultured in 80 µl of SOC medium (Sambrook et al., supra). After incubation for one hour at 37° C., the E. coli mixture was plated on Luria Bertani (LB)-agar (Sambrook et al., supra) containing 2x Carb. The following day, several colonies were randomly picked from each plate and cultured in 150 µl of liquid LB/2x Carb medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 18 µl of concentrated PCR reaction mix (3.3x) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |

| | |
|---|---|
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2, or SEQ ID NO:4 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2, or SEQ ID NO:4 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 software (National Biosciences), labeled by combining 50 pmol of each oligomer and 250 $\mu$Ci of [$\gamma$-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR film (Kodak, Rochester, N.Y.) is exposed to the blots, or the blots are exposed in a Phosphoimager cassette (Molecular Dynamics, Sunnyvale, Calif.), hybridization patterns are compared visually.

VII Microarrays

To produce oligonucleotides for a microarray, one of the nucleotide sequences of the present invention are examined using a computer algorithm which starts at the 3' end of the nucleotide sequence. The algorithm identified oligomers of defined length that are unique to the gene, have a GC content within a range suitable for hybridization, and lack predicted secondary structure that would interfere with hybridization. The algorithm identifies approximately 20 sequence-specific oligonucleotides of 20 nucleotides in length (20-mers). A matched set of oligonucleotides are created in which one nucleotide in the center of each sequence is altered. This process is repeated for each gene in the microarray, and double sets of twenty 20 mers are synthesized and arranged on the surface of the silicon chip using a light-directed chemical process, such as that discussed in Chee, supra.

In the alternative, a chemical coupling procedure and an ink jet device are used to synthesize oligomers on the surface of a substrate (cf. Baldeschweiler, supra). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. A typical array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned image is examined to determine degree of complementarity and the relative abundance/expression level of each oligonucleotide sequence in the microarray.

VIII Complementary Polynucleotides

Sequence complementary to the RAPR-encoding sequence, or any part thereof, is used to decrease or inhibit expression of naturally occurring RAPR. Although use of oligonucleotides comprising from about 15 to about 30 base-pairs is described, essentially the same procedure is used with smaller or larger sequence fragments. Appropriate oligonucleotides are designed using OLIGO 4.06, software and the coding sequence of RAPR, SEQ ID NO:1 or SEQ ID NO:3. To inhibit transcription, a complementary oligonucleotide is designed from the most unique 5' sequence and used to prevent promoter binding to the coding sequence. To inhibit translation, a complementary oligonucleotide is designed to prevent ribosomal binding to the RAPR-encoding transcript.

IX Expression of RAPR

Expression of RAPR is accomplished by subcloning the cDNAs into appropriate vectors and transforming the vectors into host cells. In this case, the cloning vector is also used to express RAPR in E. coli. Upstream of the cloning site, this vector contains a promoter for $\beta$-galactosidase, followed by sequence containing the amino-terminal Met, and the subsequent seven residues of $\beta$-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of $\beta$-galactosidase, about 5 to 15 residues of linker, and the full length protein. The signal residues direct the secretion of RAPR into the bacterial growth media which can be used directly in the following assay for activity.

X Demonstration of RAPR Activity

The activity of RAPR is determined by its ability to stimulate cell growth in response to GTP. Specifically, RAPR is expressed in a mammalian cell line such as 293T by transfecting with an eukaryotic expression vector encoding RAPR. A second construct which expresses any one of a number of reporter genes such as $\beta$-galactosidase is co-transformed into the cells in order to allow rapid identification of those cells which have taken up and expressed the RAPR-containing DNA. Transformed cells expressing $\beta$-galactosidase are stained blue when a suitable colorimetric substrate is added to the culture media under conditions that are well known in the art. After transformation, the co-transformed cells are cultured in a defined synthetic medium with GTP for 48 hours to allow expression and accumulation of RAPR and $\beta$-galactosidase. As a control, cells are transformed with the same reporter construct but not with the RAPR expression vector and are cultured under the same conditions. RAPR activity is indicated by increased growth of the cells which contain the RAPR expression vector in response to GTP in comparison to the control cells (Ren, M. et al. (1996) Proc. Natl. Acad. Sci. 93:5151–5155).

XI Production of RAPR Specific Antibodies

RAPR that is substantially purified using PAGE electrophoresis (Sambrook, supra), or other purification techniques, is used to immunize rabbits and to produce antibodies using standard protocols. The amino acid sequence deduced from SEQ ID NO:2 or SEQ ID NO:4, is analyzed using DNAS-TAR software (DNASTAR Inc.) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 431A peptide synthesizer using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring RAPR Using Specific Antibodies

Naturally occurring or recombinant RAPR is substantially purified by immunoaffinity chromatography using antibodies specific for RAPR. An immunoaffinity column is constructed by covalently coupling RAPR antibody to an activated chromatographic resin, such as CNBr-activated SEPHAROSE (Pharmacia & Upjohn). After the coupling, the resin is blocked and washed according to the manufacturer's instructions.

Media containing RAPR is passed over the immunoaffinity column, and the column is washed under conditions that allow the preferential absorbance of RAPR (e.g., high ionic strength buffers in the presence of detergent). The column is eluted under conditions that disrupt antibody/RAPR binding (eg, a buffer of pH 2–3 or a high concentration of a chaotrope, such as urea or thiocyanate ion), and RAPR is collected.

XIII Identification of Molecules Which Interact with RAPR

RAPR or biologically active fragments thereof are labeled with $^{125}$I Bolton-Hunter reagent (Bolton et al. (1973) Biochem. J. 133:529). Candidate molecules previously arrayed in the wells of a multi-well plate are incubated with the labeled RAPR, washed and any wells with labeled RAPR complex are assayed. Data obtained using different concentrations of RAPR are used to calculate values for the number, affinity, and association of RAPR with the candidate molecules.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A substantially purified Ras protein (RAPR) comprising an amino acid sequence selected from the group consisting of SEQ ID NO:1 or SEQ ID NO:3.

2. An isolated and purified polynucleotide encoding the RAPR of claim 1.

3. A composition comprising the polynucleotide sequence of claim 2.

4. An isolated and purified polynucleotide which is complementary to the polynucleotide sequence of claim 2.

5. An isolated and purified polynucleotide comprising a polynucleotide sequence selected from the group consisting of SEQ ID NO:2 or SEQ ID NO:4.

6. An isolated and purified polynucleotide which is complementary to the polynucleotide sequence of claim 5.

7. An expression vector containing the polynucleotide of claim 2.

8. A host cell containing the expression vector of claim 7.

9. A method for producing a polypeptide comprising the amino acid sequence of SEQ ID NO:1 or SEQ ID NO:3, the method comprising the steps of:

a) culturing the host cell of claim 8 under conditions suitable for the expression of the polypeptide; and b) recovering the polypeptide from the host cell culture.

10. A pharmaceutical composition comprising the RAPR of claim 1 in conjunction with a suitable pharmaceutical carrier.

11. A method for preventing or treating a disorder associated with an increase in apoptosis comprising administering to a subject in need of such treatment an effective amount of the pharmaceutical composition of claim 10.

12. A method for detecting a polynucleotide encoding RAPR in a biological sample containing nucleic acids, the method comprising the steps of:

(a) hybridizing the polynucleotide of claim 4 to at least one of the nucleic acids in the biological sample, thereby forming a hybridization complex; and (b) detecting the hybridization complex, wherein the presence of the hybridization complex correlates with the presence of a polynucleotide encoding RAPR in the biological sample.

13. The method of claim 12 wherein the nucleic acids of the biological sample are amplified by the polymerase chain reaction prior to hybridization.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 249 amino acids
        (B) TYPE: amino acid
        (C) STRANDEDNESS: single
        (D) TOPOLOGY: linear (vii) IMMEDIATE SOURCE:
        (A) LIBRARY: TLYMNOT01
        (B) CLONE: 143362

(xi) SEQUENCE DESCRIPTION: SEQ ID NO:1:

Met Val Gly Leu Asp Asn Ala Gly Lys Thr Ala Thr Ala Lys Gly Ile
1               5                   10                  15

Gln Gly Glu Tyr Pro Glu Asp Val Ala Pro Thr Val Gly Phe Ser Lys
            20                  25                  30

Ile Asn Leu Arg Gln Gly Lys Phe Glu Val Thr Ile Phe Asp Leu Gly
        35                  40                  45

Gly Gly Ile Arg Ile Arg Gly Ile Trp Lys Asn Tyr Tyr Ala Glu Ser
    50                  55                  60

Tyr Gly Val Ile Phe Val Val Asp Ser Ser Asp Glu Glu Arg Met Glu
65                  70                  75                  80

Glu Thr Lys Glu Ala Met Ser Glu Met Leu Arg His Pro Arg Ile Ser
                85                  90                  95

```
Gly Lys Pro Ile Leu Val Leu Ala Asn Lys Gln Asp Lys Glu Gly Ala
            100                 105                 110

Leu Gly Glu Ala Asp Val Ile Glu Cys Leu Ser Leu Glu Lys Leu Val
        115                 120                 125

Asn Glu His Lys Cys Leu Cys Gln Ile Glu Pro Cys Ser Ala Ile Ser
    130                 135                 140

Gly Tyr Gly Lys Lys Ile Asp Lys Ser Ile Lys Lys Gly Leu Tyr Trp
145                 150                 155                 160

Leu Leu His Val Ile Ala Arg Asp Phe Asp Ala Leu Asn Glu Arg Ile
                165                 170                 175

Gln Lys Glu Thr Thr Glu Gln Arg Ala Leu Glu Glu Gln Glu Lys Gln
            180                 185                 190

Glu Arg Ala Glu Arg Val Arg Lys Leu Arg Glu Arg Lys Gln Asn
        195                 200                 205

Glu Gln Glu Gln Ala Glu Leu Asp Gly Thr Ser Gly Leu Ala Glu Leu
    210                 215                 220

Asp Pro Glu Pro Thr Asn Pro Phe Gln Pro Ile Ala Ser Val Ile Ile
225                 230                 235                 240

Glu Asn Glu Gly Lys Lys Arg Arg Ile
                245
```

(2) INFORMATION FOR SEQ ID NO:2:

(i) SEQUENCE CHARACTERISTICS:
        (A) LENGTH: 1619 base pairs
        (B) TYPE: nucleic acid
        (C) STRANDEDNESS: single
        (D) TOPOLOGY: linear (vii) IMMEDIATE SOURCE:
        (A) LIBRARY: TLYMNOT01
        (B) CLONE: 143362

(xi) SEQUENCE DESCRIPTION: SEQ ID NO:2:

```
CCTACACGCT TCCGCCCACG CGTCCGCCCA CGCGTCCGCT TTAGCCGGGT CCCGCTAACT    60

CGGCTACGGT GTATCTGCGT CTTTGGTCAG GTTGTTCCTT GGCTAAGAGG GCAGTCGTCG   120

CGGACCCACG CGGTTAGCAA GGCTTAGTGC TCGGGCCGGC CGCCTTCACT TCCCTCCCGG   180

CTTTTCCTCC CGACTTATCC ACTTTAGGGG CGTCTCGGAG TGCCGGAGCC CCCGGGGAAG   240

AGCGGGGTGC CGGTGTCCGC TCCGGGCTCG GATGGGAAGT GGTGGGAGGA GCGACCCGGG   300

ATGTTCAGTC TGATGGCCAG TTGCTGCGGC TGGTTCAAGC GGTGGCGGGA GCTGTCAGAA   360

AGGTGACTCT TTTGATGGTG GGACTTGATA ATGCTGGTAA AACCGCAACA GCAAAGGGAA   420

TCCAAGGAGA ATACCCTGAA GATGTAGCTC CTACTGTTGG ATTTTCAAAA ATTAACCTTA   480

GACAAGGAAA GTTTGAAGTC ACCATCTTTG ACTTGGGAGG TGGAATAAGA ATTCGGGGAA   540

TCTGGAAGAA TTACTATGCT GAATCCTATG GGGTAATATT TGTTGTGGAT TCCAGTGATG   600

AAGAGAGAAT GGAAGAGACA AAAGAGGCTA TGTCAGAAAT GCTAAGACAT CCTAGGATAT   660

CGGGAAAGCC TATATTGGTG TTGGCAAATA AACAAGATAA AGAAGGAGCT TTAGGAGAAG   720

CTGATGTCAT TGAATGTCTA TCTCTGGAAA AATTGGTCAA TGAGCACAAG TGCCTGTGTC   780

AGATAGAACC ATGTTCAGCA ATCTCGGGGT ATGGAAAGAA AATTGACAAG TCCATTAAAA   840

AAGGCCTTTA TTGGCTGCTA CATGTTATTG CAAGAGACTT TGATGCCTTA AATGAACGCA   900

TCCAAAAAGA GACAACAGAG CAGCGTGCTC TTGAGGAACA AGAAAACAA GAAAGAGCTG   960

AACGAGTGCG AAAATTACGA GAAGAAAGAA AACAAAATGA ACAGGAGCAG GCTGAACTCG  1020

ATGGAACCAG TGGTCTGGCT GAGTTGGACC CAGAACCAAC GAATCCTTTC CAGCCAATAG  1080
```

-continued

```
CATCTGTAAT CATTGAGAAT GAAGGAAAAA AAAGGAGGAT CTAAAAAAAA AAAGGGGGGG      1140

CCCCCCTTTT TTTTTTTTTT TTTTTGGGGG GGGGGATTTC CCCCTTGTGG GGTTTTTTTT      1200

TGGGGGGGGG GGGCCAAGCC AAAAAAATGG TTCCCCACAC CGGGGGCATA AAGAATCCCC      1260

CCCGCCTGTT GGGAGAAACA AGGGGGGCCC CCGGGGGGGT TTTTTGGGG GAAAAAAATT      1320

CCCCCCCCCG GGAGGGGATA TTTTCCCGCC CCGGGGTGGG GGGCAAGACG CCCCCGATTG      1380

NAGGNCNCGG TGTGCGTTNT TGTGGTTGGT TGTTGTGTAG AGAGCGCCCC TCCGGAGGAG      1440

GAGAGAGGCG CCGCCCGCGC GGTGGTGGTT CCTCCTCTGT GTGGTTGTTT TGGAGAGGGA      1500

AGGGGTGCTG CCCCGTGTCG CGCGAAGAAA GCTGGCCTGC TGGAGGCTGT TTGTTAATGA      1560

ACGCTGGGGG GGGGGGTGGG GGGGCGTGAG TGGTGGCCCC GCGGAACTTC CCACCAGGG      1619
```

(2) INFORMATION FOR SEQ ID NO:3:

(i) SEQUENCE CHARACTERISTICS:
        (A) LENGTH: 211 amino acids
        (B) TYPE: amino acid
        (C) STRANDEDNESS: single
        (D) TOPOLOGY: linear (vii) IMMEDIATE SOURCE:
        (A) LIBRARY: COLNNOT01
        (B) CLONE: 607908

(xi) SEQUENCE DESCRIPTION: SEQ ID NO:3:

```
Met Asp Ala Pro Gly Ala Leu Ala Gln Thr Ala Ala Pro Gly Pro Gly
 1               5                  10                  15

Arg Lys Glu Leu Lys Ile Val Ile Val Gly Asp Gly Gly Cys Gly Lys
             20                  25                  30

Thr Ser Leu Leu Met Val Tyr Ser Gln Gly Ser Phe Pro Glu His Tyr
         35                  40                  45

Ala Pro Ser Val Phe Glu Lys Tyr Thr Ala Ser Val Thr Val Gly Ser
     50                  55                  60

Lys Glu Val Thr Leu Asn Leu Tyr Asp Thr Ala Gly Gln Glu Asp Tyr
65                  70                  75                  80

Asp Arg Leu Arg Pro Leu Ser Tyr Gln Asn Thr His Leu Val Leu Ile
                 85                  90                  95

Cys Tyr Asp Val Met Asn Pro Thr Ser Tyr Asp Asn Val Leu Ile Lys
            100                 105                 110

Trp Phe Pro Glu Val Thr His Phe Cys Arg Gly Ile Pro Met Val Leu
        115                 120                 125

Ile Gly Cys Lys Thr Asp Leu Arg Lys Asp Lys Glu Gln Leu Arg Lys
    130                 135                 140

Leu Arg Ala Ala Gln Leu Glu Pro Ile Thr Tyr Met Gln Gly Leu Ser
145                 150                 155                 160

Ala Cys Glu Gln Ile Arg Ala Ala Leu Tyr Leu Glu Cys Ser Ala Lys
                165                 170                 175

Phe Arg Glu Asn Val Glu Asp Val Phe Arg Glu Ala Ala Lys Val Ala
            180                 185                 190

Leu Ser Ala Leu Lys Lys Ala Gln Arg Gln Lys Lys Arg Arg Leu Cys
        195                 200                 205

Leu Leu Leu
    210
```

(2) INFORMATION FOR SEQ ID NO:4:

(i) SEQUENCE CHARACTERISTICS:

(A) LENGTH: 1543 base pairs
(B) TYPE: nucleic acid
(C) STRANDEDNESS: single
(D) TOPOLOGY: linear (vii) IMMEDIATE SOURCE:
(A) LIBRARY: COLNNOT01
(B) CLONE: 607908

(xi) SEQUENCE DESCRIPTION: SEQ ID NO:4:

```
GCGCGCCGCC GCCAGTGCTG CGGGCTCCGG GCAATGGATG CCCCCGGGGC CCTGGCCCAG        60
ACCGCCGCCC CCGGTCCGGG CAGGAAGGAG CTGAAGATCG TGATCGTGGG CGACGGCGGC       120
TGCGGCAAGA CCTCGCTGCT CATGGTGTAC AGCCAGGGCT CCTTCCCCGA GCACTACGCC       180
CCATCGGTGT TCGAGAAGTA CACGGCCAGC GTGACCGTTG GCAGCAAGGA GGTGACCCTG       240
AACCTCTACG ACACGGCCGG GCAAGAAGAC TATGACCGGC TGCGGCCCCT GTCCTACCAG       300
AACACCCACC TCGTGCTCAT CTGCTATGAC GTCATGAATC CCACCAGCTA CGACAACGTC       360
CTCATCAAGT GGTTCCCTGA GGTCACGCAT TTCTGCCGCG GGATCCCCAT GGTGCTCATC       420
GGCTGCAAGA CAGACCTGAG GAAGGACAAG GAGCAGCTGC GGAAGCTCCG GGCCGCCCAG       480
CTGGAGCCCA TCACCTACAT GCAGGGCCTG AGCGCCTGCG AACAGATCCG AGCTGCTCTC       540
TACCTGGAAT GTTCCGCCAA GTTTCGGAG AATGTGGAGG ACGTCTTCCG GGAGGCCGCC       600
AAGGTGGCTC TCAGCGCTCT GAAGAAGGCG CAACGGCAGA AGAAGCGCCG GCTCTGCCTG       660
CTGCTCTGAC CCAGGGCAGA CAGACCTCAC GACAGCACTG ACAGGGGCCC GGGGGCCCAG       720
GTGCCGATTG CACCAGGGAG GCTGCCCCAC CCCGACCCTC CAGCTCATGG TGTCTGGGGC       780
CTGCGGCTAG ACTCTTGGAA CATTCTGGGA ACTCTCTCCT CCCCCGGCTG GGGCTTTGAC       840
CAANAAACTC CCCTCCAGGC TGCCCCTGGG ACAATGGGTT GGTGAATGTT GGGTTCAAGG       900
AGNCCAAGTG TTTTGTTGTT GGGACCTTTG AAAAGTGGNC CTTAAATTCA AAAAGGCCAA       960
ACCNNNAAAN CAAAAGGAGT TGTTTTTCCC CCAAAAGTTG AAAAGGNNTT NAAAAGTTAA      1020
TTGNTTTTTN AAAAAATNGA AAAAAAAAGG NNTTAAATTN TTNGGNAAAA GTTGGGGAAA      1080
AAAANGGTAA GGACCCCTTT GGGGAAAATT TNTTTTCCAA AAGGGGGGGG NNNGGGNCCC      1140
CAAAAAAGGN NNTTTTTNCA GNAGCCAGCG CACTGNTGNT CGTTTTTTTT TTTTTTTTT      1200
TCATCACAGG CACCCCCCAC CNTNNAGTTT TCTTCCCACG NGNNAGATTT AAGCTTATNT      1260
TCGNAANTNA ANANNNTNCT NTNTTNGNTA GGGGCTNTAC CNTTGATCTT TTTAATTTCC      1320
CCANNCTNGA NTCNTTTTTT CTNCCATTTN CTTTTTTTCT TTTTCCTCGN GTTNCNCTNT      1380
TTNNCNNCAC TTTTTTCCCA TTTTCTCCTT CTTTCCCNAT NATAATTANA NCTCCGAAGG      1440
GGNTTTACT TTNTTATNCA ATAATCTTTT GCATCAATTA NNCCCCTTTN TCACCCTCTC      1500
ATCCTATTTN CCCTTCNCTC TNNTTTNNTT CTCNNNNGNC ATC                       1543
```

(2) INFORMATION FOR SEQ ID NO:5:

(i) SEQUENCE CHARACTERISTICS:
(A) LENGTH: 184 amino acids
(B) TYPE: amino acid
(C) STRANDEDNESS: single
(D) TOPOLOGY: linear (vii) IMMEDIATE SOURCE:
(A) LIBRARY: GenBank
(B) CLONE: 2062133

(xi) SEQUENCE DESCRIPTION: SEQ ID NO:5:

```
Met Gly Leu Leu Thr Ile Leu Lys Lys Met Lys Gln Lys Glu Arg Asp
 1               5                  10                  15
```

```
Val Arg Leu Leu Met Leu Gly Leu Asp Asn Ala Gly Lys Thr Thr Ile
         20                  25                  30

Leu Lys Lys Phe Asn Gly Glu Asp Val Asp Thr Ile Ser Pro Thr Leu
         35                  40                  45

Gly Phe Asn Ile Lys Thr Leu Glu His Arg Gly Phe Lys Leu Asn Ile
 50                  55                  60

Trp Asp Val Gly Gly Gln Lys Ser Leu Arg Ser Tyr Trp Arg Asn Tyr
 65                  70                  75                  80

Phe Glu Ser Thr Asp Gly Leu Ile Trp Val Asp Ser Ala Asp Arg
                 85                  90                  95

Gln Arg Met Gln Asp Cys Gln Arg Glu Leu Gln Ser Leu Leu Val Glu
                100                 105                 110

Glu Arg Leu Ala Gly Ala Thr Leu Leu Ile Phe Ala Asn Lys Gln Asp
                115                 120                 125

Leu Pro Gly Ala Leu Ser Cys Asn Ala Ile Gln Glu Ala Leu Glu Leu
        130                 135                 140

Asp Ser Ile Arg Ser His His Trp Arg Ile Gln Gly Cys Ser Ala Val
145                 150                 155                 160

Thr Gly Glu Asp Leu Leu Pro Gly Ile Asp Trp Leu Leu Asp Asp Ile
                165                 170                 175

Ser Ser Arg Val Phe Thr Ala Asp
        180

(2) INFORMATION FOR SEQ ID NO:6:

(i) SEQUENCE CHARACTERISTICS:
        (A) LENGTH: 210 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1702943

(xi) SEQUENCE DESCRIPTION: SEQ ID NO:6:

Met Asn Ala Ser Gln Val Ala Gly Glu Glu Ala Pro Gln Ser Gly His
 1               5                  10                  15

Ser Val Lys Val Val Leu Val Gly Asp Gly Gly Cys Gly Lys Thr Ser
         20                  25                  30

Leu Met Met Val Phe Ala Lys Gly Ala Phe Pro Glu Ser Tyr Ser Pro
         35                  40                  45

Thr Val Phe Glu Arg Tyr Asn Ala Thr Leu Gln Met Lys Gly Lys Pro
 50                  55                  60

Val His Leu Gln Ile Trp Asp Thr Ala Gly Gln Asp Tyr Asp Arg
 65                  70                  75                  80

Leu Arg Pro Leu Phe Tyr Pro Asp Ala Asn Val Leu Leu Leu Cys Phe
                 85                  90                  95

Asp Val Thr Asn Pro Asn Ser Phe Asp Asn Val Ser Asn Arg Trp Tyr
                100                 105                 110

Pro Glu Val Thr His Phe Cys Lys Gly Val Pro Ile Ile Val Val Gly
                115                 120                 125

Cys Lys Ile Asp Leu Arg Lys Asp Lys Val Leu Val Asn Asn Leu Arg
        130                 135                 140

Lys Lys Arg Leu Glu Pro Val Thr Tyr His Arg Gly His Asp Met Ala
145                 150                 155                 160

Arg Ser Val Gly Ala Val Ala Tyr Leu Glu Cys Ser Ala Arg Leu His
```

```
                   165                 170                 175
Asp Asn Val Glu Ala Val Phe Gln Glu Ala Ala Glu Val Ala Leu Ser
            180                 185                 190

Ser Arg Arg His Asn Phe Trp Arg Arg Ile Thr Gln Asn Cys Cys Leu
        195                 200                 205

Ala Thr
    210
```